(12) United States Patent
Hitson (10) Patent No.: US 7,918,337 B2
(45) Date of Patent: Apr. 5, 2011

(54) PHARMACEUTICAL WASTE CONTAINER SYSTEM

(76) Inventor: Tamara Hitson, Richmond, IN (US)

( * ) Notice: Subject to any disclaimer, the term of this patent is extended or adjusted under 35 U.S.C. 154(b) by 13 days.

(21) Appl. No.: 12/472,867

(22) Filed: May 27, 2009

(65) Prior Publication Data

US 2009/0294312 A1     Dec. 3, 2009

Related U.S. Application Data

(60) Provisional application No. 61/056,659, filed on May 28, 2008.

(51) Int. Cl.
- *B65F 1/16* (2006.01)
- *B65D 83/10* (2006.01)
- *B65D 81/24* (2006.01)
- *A47G 29/00* (2006.01)

(52) U.S. Cl. ..... 206/366; 206/205; 206/370; 220/908.3; 232/43.3

(58) Field of Classification Search .......... 206/205, 206/366, 370; 220/501–502, 908, 908.3; 232/43.1–43.5
See application file for complete search history.

(56) References Cited

U.S. PATENT DOCUMENTS

| | | | | |
|---|---|---|---|---|
| 2,661,747 A | * | 12/1953 | Manion | 220/502 |
| 2,989,964 A | * | 6/1961 | Willett | 220/502 |
| 3,651,817 A | * | 3/1972 | Baker | 220/502 |
| 3,750,966 A | | 8/1973 | Anderson | |
| 4,804,090 A | * | 2/1989 | Schuh et al. | 206/366 |
| 4,961,541 A | | 10/1990 | Hashimoto | |
| 4,964,425 A | * | 10/1990 | Chang | 131/237 |
| 5,046,614 A | * | 9/1991 | Torres et al. | 206/366 |
| 5,209,411 A | | 5/1993 | Dineley et al. | |
| 5,483,999 A | | 1/1996 | Lampropoulos et al. | |
| 5,603,404 A | | 2/1997 | Nazare et al. | |
| 5,707,173 A | | 1/1998 | Cottone et al. | |
| 5,740,909 A | | 4/1998 | Nazare et al. | |
| 6,053,314 A | | 4/2000 | Pittman | |
| 6,186,428 B1 | | 2/2001 | Robinson et al. | |
| 6,311,909 B1 | | 11/2001 | Lin | |
| 6,357,682 B1 | | 3/2002 | Hext | |
| 6,494,391 B2 | | 12/2002 | Mosenson et al. | |
| 6,568,614 B2 | | 5/2003 | Chen et al. | |
| 6,719,017 B1 | | 4/2004 | McArthur et al. | |
| 6,854,836 B2 | | 2/2005 | Ishinaga et al. | |
| 6,889,831 B2 | * | 5/2005 | Pike | 206/366 |
| 6,923,318 B1 | * | 8/2005 | Erickson et al. | 206/366 |
| 7,032,851 B2 | | 4/2006 | Demske et al. | |
| 7,131,965 B1 | | 11/2006 | Thornbury et al. | |
| 7,174,928 B1 | | 2/2007 | Lampropoulos | |
| 7,360,730 B2 | | 4/2008 | Brown | |

(Continued)

*Primary Examiner* — Bryon P Gehman
(74) *Attorney, Agent, or Firm* — Woodard, Emhardt, Moriarty, McNett & Henry LLP (57) ABSTRACT

A pharmaceutical waste disposal device comprises an upper portion adapted for receiving pharmaceutical waste and a lower portion adapted for collecting the pharmaceutical waste, the lower portion being selectively and removably engagable with the upper portion. The upper portion includes a housing surrounding an internal rotating wheel and a lid slideably engaged with the housing. Additionally, the rotating wheel includes collection areas adapted for collecting pharmaceutical waste placed in the upper portion. The lid includes a lower pivoting flap adapted for contacting and rotating the wheel upon closing the lid to transfer the pharmaceutical waste to the lower portion. Further, the rotating wheel is sized and positioned within the housing in a manner to substantially prevent access to the pharmaceutical waste collected in the lower portion.

20 Claims, 4 Drawing Sheets

U.S. PATENT DOCUMENTS

| | | |
|---|---|---|
| 2006/0000833 A1 | 1/2006 | Boots et al. |
| 2006/0079726 A1 | 4/2006 | Lampropoulos |
| 2006/0219718 A1 | 10/2006 | Finnestad |
| 2006/0278545 A1 | 12/2006 | Henning |
| 2007/0029006 A1 | 2/2007 | Lampropoulos |
| 2007/0032764 A1 | 2/2007 | Lampropoulos |

* cited by examiner

PHARMACEUTICAL WASTE CONTAINER SYSTEM

CROSS-REFERENCE TO RELATED APPLICATIONS

This application claims the benefit of U.S. Provisional Application No. 61/056,659, filed May 28, 2008, which is hereby incorporated by reference.

FIELD OF DISCLOSURE

The present disclosure relates to the field of waste handling containers and specifically to solid and liquid pharmaceutical waste containers.

BACKGROUND OF THE DISCLOSURE

In recent years, there has been an increasing focus on the safety and environmental impact of the disposal of hazardous waste materials, and specifically pharmaceutical waste. In many medical facilities such as hospitals and nursing homes, sharps containers are utilized for the disposal of medical needles. These containers collect the disposed medical needles and then the containers themselves may be collected by approved individuals and transferred to medical waste treatment sites. However, before medical needles are disposed of within the sharps containers, often the injectable pharmaceutical liquid within the syringe is discharged down a drain within the medical facility, joining the medical facility's wastewater and possibly traveling to a wastewater treatment site. Unfortunately, wastewater treatment sites are often incapable of properly treating various types of pharmaceutical waste, thereby increasing the chance that the injectable pharmaceutical liquid will end up in a local water supply environment. Similarly, medical personnel often dispose of solid pharmaceutical waste by rinsing the waste down a drain in the medical facility, resulting in the same hazardous implications described above with respect to liquid pharmaceutical waste. Moreover, the same disposal practices are often employed in residential homes with individuals requiring liquid and solid pharmaceutical products.

It is, therefore, desired to provide one or more containers to ensure the proper and safe disposal of liquid and solid pharmaceutical waste and to lessen the environmental impact resulting from the disposal of these products.

SUMMARY OF THE DISCLOSURE

In certain embodiments, a pharmaceutical waste disposal device comprises an upper portion adapted for receiving pharmaceutical waste and a lower portion adapted for collecting the pharmaceutical waste, the lower portion being selectively and removably engagable with the upper portion. The upper portion includes a hollow housing having an interior surface defining an internal cavity, an exterior surface, a length and a width, the housing defining top and bottom openings in communication with the internal cavity. The housing is configured to selectively engage with the lower portion. Additionally, the top opening is divisible into adjacent first and second portions, the first and second portions each extending the length of the housing and collectively extending the width of the housing. The upper portion includes a rotating wheel positioned within the housing. The rotating wheel includes a plurality of paddles extending radially from a central rotating shaft, each of the paddles having a proximal edge rigidly engaged with the shaft and an opposite distal edge. Additionally, the upper portion includes a non-movable cover engaged with the housing at the top opening and positioned to cover the first portion of the top opening. The upper portion further includes a sliding lid engaged with the housing at the top opening and positioned to selectively cover the second portion of the top opening when at a closed position, the lid being configured to slide underneath the non-movable cover to an open position to reveal the second portion and provide access to the internal cavity therethrough. The sliding lid is configured to slide along the width of the housing, the sliding lid having opposing top and bottom surfaces. The upper portion further includes a flap hingedly engaged with the sliding lid adjacent the bottom surface of the lid, the flap including a pivot edge hingedly engaged with the sliding lid and an opposite free edge movable within the internal cavity. The pivot edge is positioned closer to the non-moveable cover than the free edge when at the closed position. Additionally, the flap is configured to pivot downward from the bottom surface an angular distance to a pivoted position, whereby sliding the lid from the open position toward the closed position causes the free edge to contact at least one of the paddles and urge the paddle to rotate the wheel to deposit pharmaceutical waste accumulated on the wheel into the lower portion. The lower portion includes a hollow housing defining an internal cavity and a top opening in communication with the internal cavity. The hollow housing of the lower portion is configured to selectively engage with the hollow housing of the upper portion so that the internal cavity of the upper portion is in communication with the internal cavity of the lower portion when the top and lower portions are engaged.

In certain other embodiments, a method comprises sliding open the lid of a pharmaceutical waste container, the waste container having an upper portion for receiving pharmaceutical waste and a lower portion for collecting the pharmaceutical waste. The upper portion of the container has an internal rotating wheel, the lid being selectively engageable with the wheel such that sliding the lid closed operates to rotate the wheel. The method further includes depositing pharmaceutical waste into the upper portion of the waste container and sliding the lid of the waste container closed, thereby rotating the wheel to transfer the deposited pharmaceutical waste into the lower portion of the container.

In yet other embodiments, a pharmaceutical waste disposal device comprises an upper portion adapted for receiving pharmaceutical waste and a lower portion adapted for collecting the pharmaceutical waste, the lower portion being selectively and removably engagable with the upper portion. The upper portion includes a housing surrounding an internal rotating wheel and a lid slideably engaged with the housing. Additionally, the rotating wheel includes collection areas adapted for collecting pharmaceutical waste placed in the upper portion. The lid includes a lower pivoting flap adapted for contacting and rotating the wheel upon closing the lid to transfer the pharmaceutical waste to the lower portion. Further, the rotating wheel is sized and positioned within the housing in a manner to substantially prevent access to the pharmaceutical waste collected in the lower portion.

DESCRIPTION OF THE ILLUSTRATED EMBODIMENTS

For the purposes of promoting an understanding of the principles of the disclosure, reference will now be made to the embodiment illustrated in the drawings and specific language will be used to describe the same. It will nevertheless be understood that no limitation of the scope of the disclosure is thereby intended, and alterations and modifications in the illustrated device, and further applications of the principles of the disclosure as illustrated therein are herein contemplated as would normally occur to one skilled in the art to which the disclosure relates.

Figure 3:
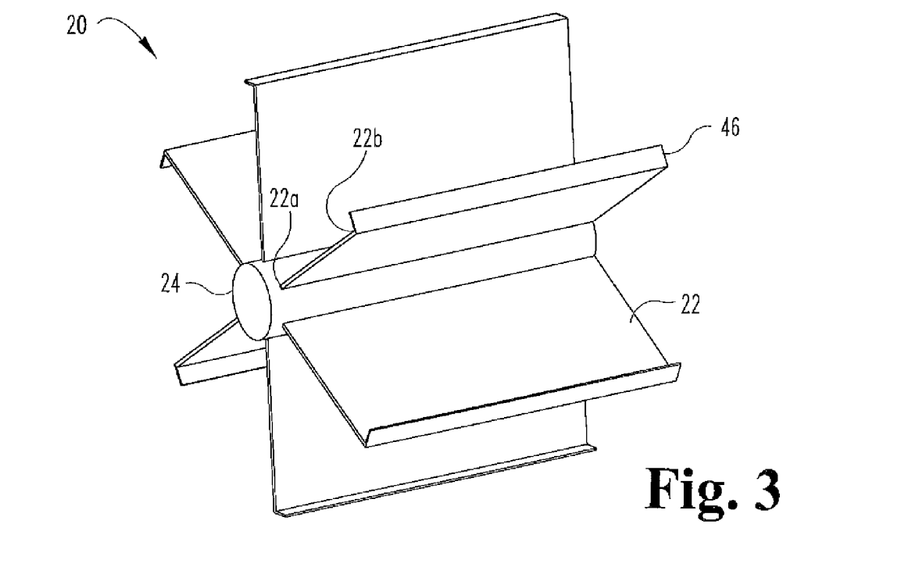
FIG. 3 is a perspective view of a component of the waste handling container of FIG. 1.
Figure 4:
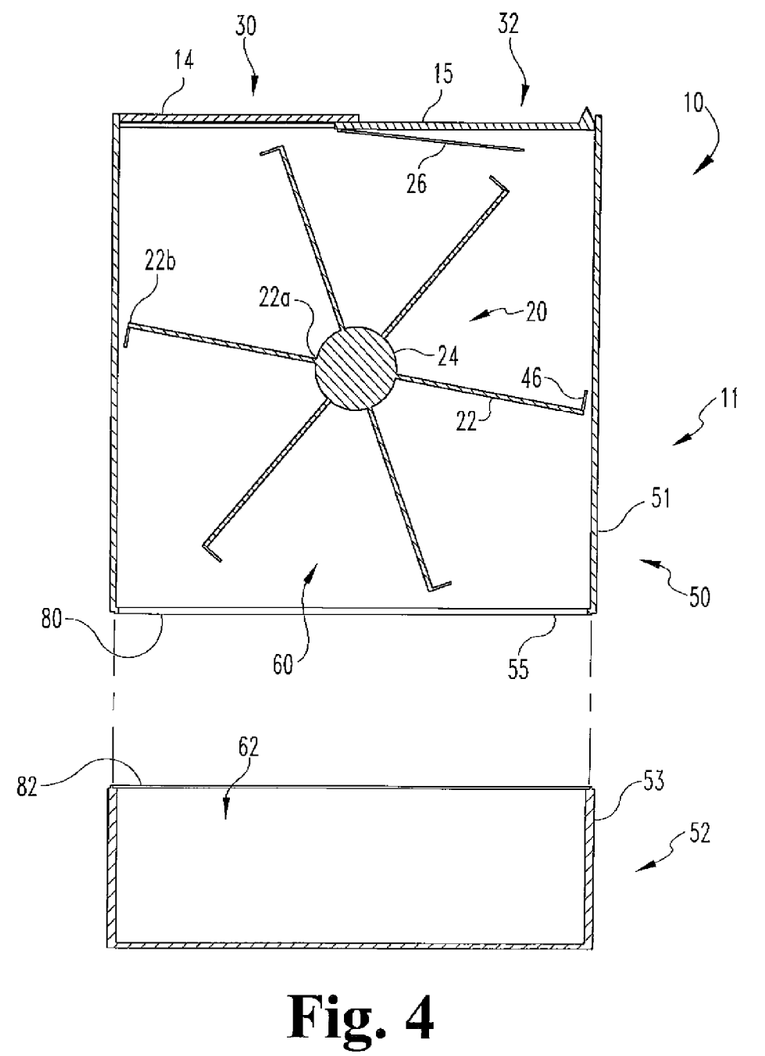
FIG. 4 is a side cross-sectional view of the waste handling container of FIG. 1.
Figure 4A:
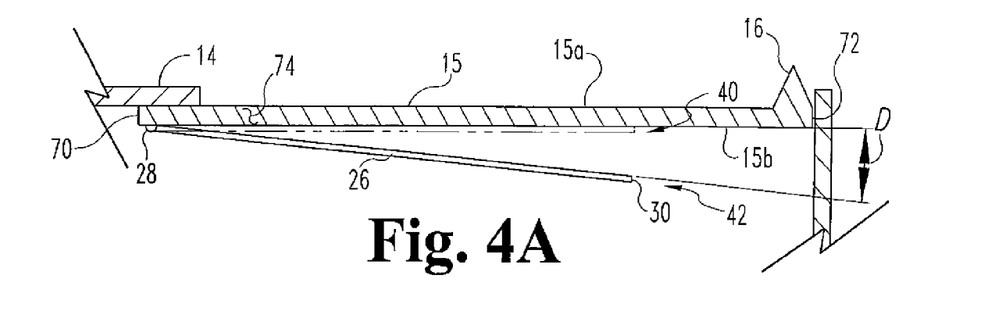
FIG. 4A is a side cross-sectional view of a portion of the waste handling container of FIG.
Figure 5A:
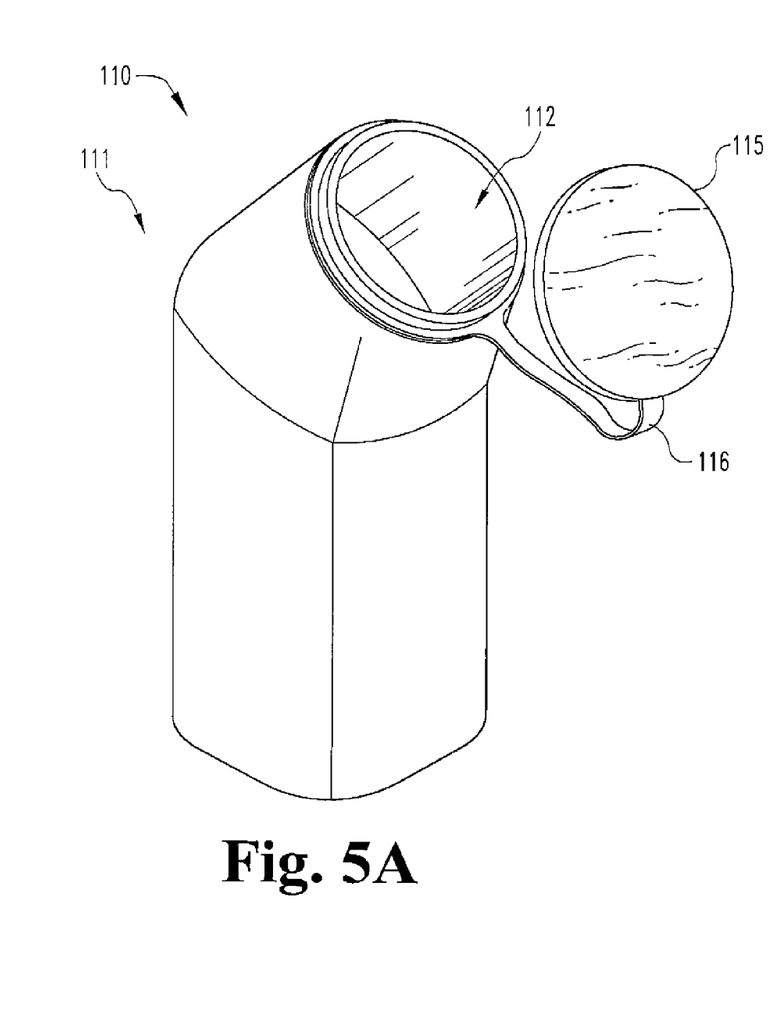
FIGS. 5A and 5B are perspective views of another waste handling container in accordance with an embodiment of the present disclosure.
Figure 5B:
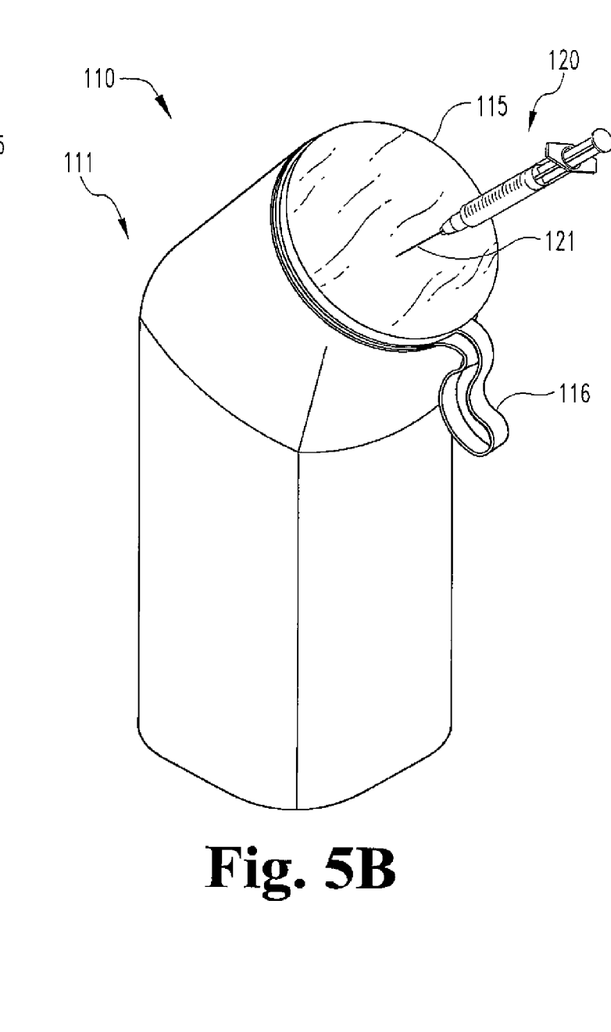

Referring generally to FIGS. 1 through 5B, components of a pharmaceutical waste container system are shown. More specifically, FIGS. 1 through 4A illustrate one embodiment of a solid waste container 10 and FIGS. 5A and 5B illustrate one embodiment of a liquid waste container 110. It is contemplated that containers 10 and 110 can be positioned together in a combined, collective and complete waste container system or can be used separately. Although the illustrations show the containers separately, it should be appreciated that in some embodiments, containers 10 and 110 may be formed together as a single unit or otherwise connectable together.

Figure 1:
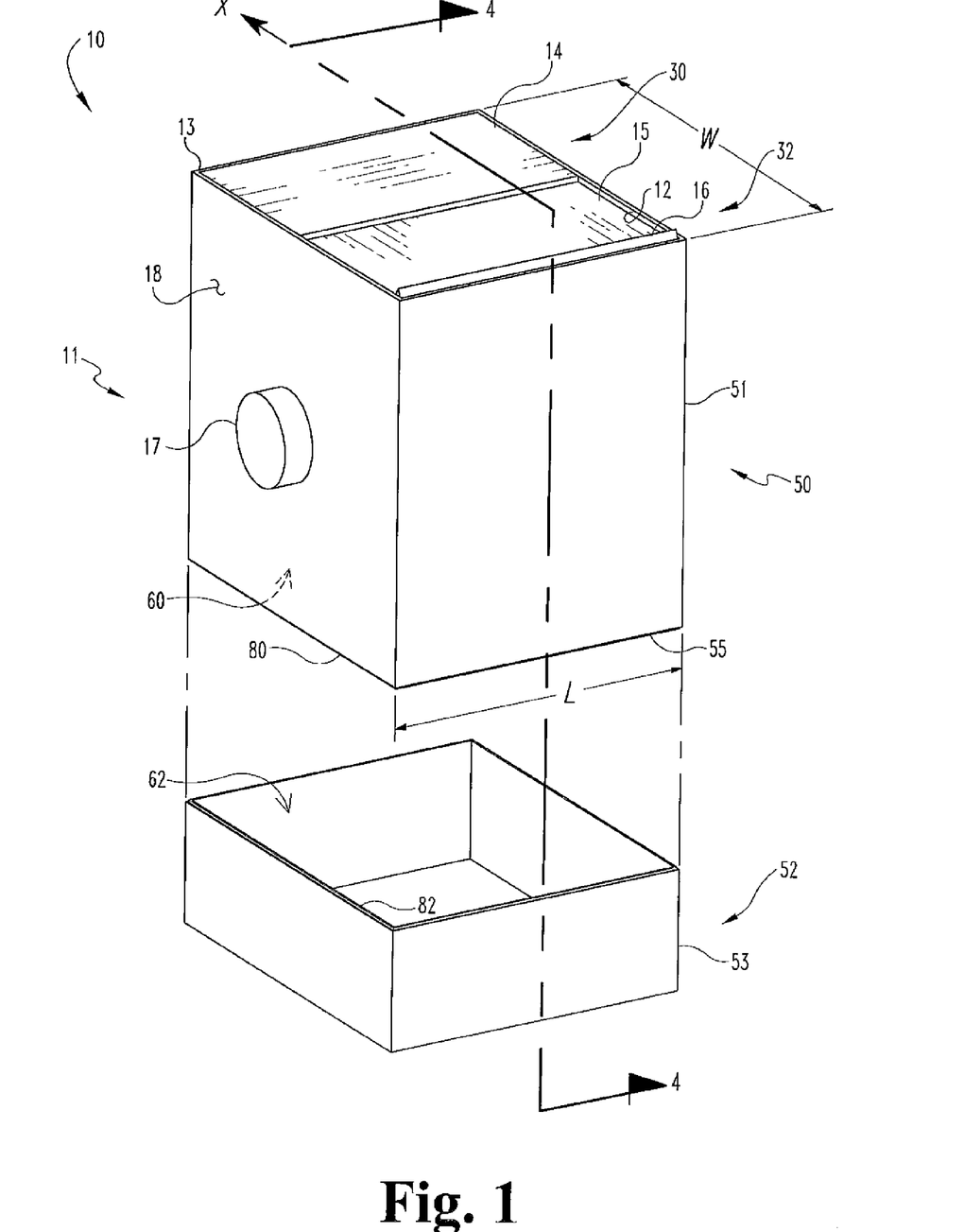
FIG. 1 is a perspective view of a waste handling container in accordance with an embodiment of the present disclosure.

Referring to FIG. 1, the illustrated container 10 generally includes a container body 11 having an upper portion 50 and a selectively removable lower portion 52 meeting at a joint 55. The upper and lower portions include hollow housings 51 and 53 defining internal cavities 60 and 62, respectively. Additionally, top portion 50 includes a top edge 13 which defines a top opening 12 through which a user can deposit solid pharmaceutical waste. In the illustrated embodiment, container 10 further includes an optional non-movable cover 14 positioned across substantially half of opening 12 and a sliding lid 15 positioned across substantially the other half of opening 12 to slideably provide access to opening 12. Container 10 also includes an optional knob 17 positioned on a side exterior surface 18 of container body 11, the knob being configured to rotate a wheel positioned within container body 11. In certain embodiments, container 10 is adapted to rest on a substantially flat support surface. Container 10 is configured to receive solid pharmaceutical waste materials through opening 12 by allowing for the user to slide lid 15 along sliding axis X when desired to expose part of opening 12, thereby exposing part of internal cavity 60, deposit one or more solid pharmaceutical waste items, such as tablets and capsules, into container body 11 to dispose of the pharmaceutical waste, and slide lid 15 to close opening 12.

In the illustrated embodiment, container body 11 is rectangular in shape, with housings 51 and 53 having length L and perpendicular width W. Additionally, as illustrated, opening 12, cover 14, and lid 15 may also be rectangular in shape. However, it should be appreciated that these elements may be shaped differently as would generally occur to one skilled in the art. Further, it is contemplated that container 10 may be sized and proportioned differently as would generally occur to one skilled in the art.

As shown in FIG. 4A, sliding lid 15 includes a top surface 15a, an opposing bottom surface 15b, a proximal edge 70, an opposing distal edge 72 and opposing sliding edges 74 extending between the proximal and distal edge of the lid. As illustrated, sliding lid 15 is arranged such that proximal edge 70 is positioned closer to non-movable cover 14 than distal edge 72. In certain embodiments, edges 74 of lid 15 may be configured to slide within channels defined in the inside of housing 51 of container body 11 along width W. In certain other embodiments, a pair of guide rail assemblies are mounted to the inside of housing 51 of container body 11 along opposite sides of opening 12 along width W, and lid 15 includes a corresponding pair of roller units mounted on each sliding edge 74 for movement within the guide rails assemblies. However, it should be appreciated that lid 15 may be configured to slide or translate with respect to housing 51 in other appropriate manners as would occur to one of ordinary skill in the art. Additionally, lid 15 may optionally include a handle 16 for holding, guiding, and generally enabling the nearly effortless opening and closing of lid 15 as desired.

Figure 2:
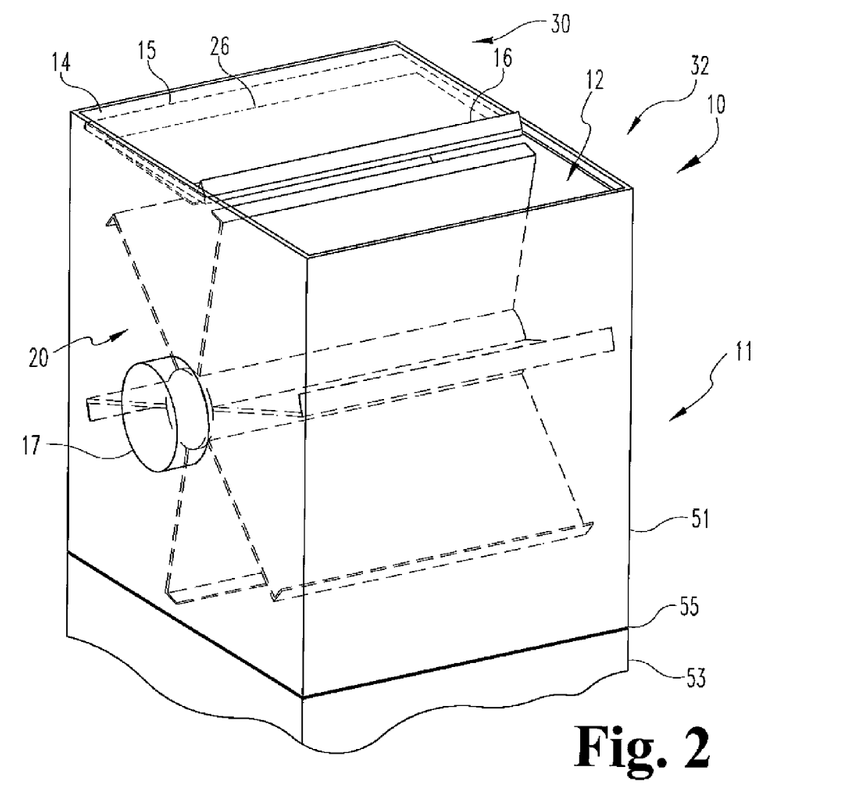
FIG. 2 is another perspective view of the waste handling container of FIG. 1.

As mentioned above, in the illustrated embodiment container 10 includes an optional stationary or non-movable cover 14 which is configured to be non-moveably engaged with housing 51 of container body 11. In certain embodiments, opening 12 may be divisible first and second adjacent portions 30 and 32, respectively, with cover 14 occupying first portion 30 and sliding lid 15 occupying second portion 32 when closed. In the illustrated embodiment, cover 14 and lid 15 are arranged such that lid 15 slides under cover 14 to an open position, thereby exposing second portion 32 of opening 12 and allowing for access to the interior of container body 11. It should be appreciated that the lid and/or cover to the container may be configured in a variety of other possible ways as would generally occur to one skilled in the art, so long as selective access to the interior of container body 11 through opening 12 is permitted. To list a few alternative examples, the container could include a removable lid, swinging door(s), or a non-movable cover defining a relatively small hole configured for the passage of solid pharmaceutical waste. In yet other alternative embodiments, a lid or cover to the container is absent such that the opening is always exposed. In even other alternative embodiments, the non-moveable cover is absent and only a single sliding lid is engaged with the top of the container body As illustrated in FIGS. 2, 3 and 4, container 10 may also include a rotating wheel 20 positioned within housing 51 for collecting pharmaceutical waste and moving the solid pharmaceutical waste deposited through opening 12 to lower portion 52, while also substantially preventing access through opening 12 to the solid pharmaceutical waste accumulated in lower portion 52. In the illustrated embodiment, wheel 20 generally includes a plurality of paddles 22 radially and rigidly disposed about a central turning shaft or rod 24. As shown, the adjacent paddles and the central turning rod create a plurality of collection areas to collect the pharmaceutical waste. It is contemplated that the paddles 22 may be rigidly attached to turning rod 24 in a variety of possible manners as would generally occur to one of ordinary skill in the art. In the illustrated embodiment, there are six paddles 22 equidistantly positioned about rod 24. It should be appreciated that paddles 22 can be sized and configured differently than as illustrated, and can number more or less than six, as would generally occur to one skilled in the art. In certain embodiments, each paddle 22 includes a proximal edge 22a rigidly engaged with the rod 42 and an opposite distal edge 24b (see FIG. 4). In certain embodiments, knob 17 may be operatively coupled with rod 24 whereby turning knob 17 operates to turn wheel 20 to allow a user to manually rotate wheel 20 as desired.

In certain embodiments, wheel 20 may be sized and configured to substantially extend the width and length of internal cavity 60 of housing 51 to substantially prevent access to the deposited pharmaceutical waste in bottom portion 52. In such cases, paddles 22 may extend out from rod 24 a sufficient distance within the interior of container body 11 to prevent access to the deposited waste at the bottom of the container body, while still providing sufficient clearance to allow the paddles to rotate within the container body. More specifically, in some embodiments, paddles 22 may each include a length substantially equal to the length of housing 51 and the distance from the distal edge 22b of one paddle 22 to the distal edge 22b of the radially opposite paddle 22 is substantially equal to the width of housing 51. In certain embodiments, paddles 22 may fully extend to the interior wall surfaces of the container body, and may include rubber tips on the ends and edges of the paddles to allow the paddles to slide along the interior wall surfaces, creating a sealed environment between the opening of the container body and the bottom of the container.

Additionally, container 10 may also include a flap 26 positioned adjacent the underside of the lid 15, the flap being configured to engage at least one of paddles 22 and rotate wheel 20 when lid 15 is closed, thereby transferring the solid pharmaceutical waste deposited through opening 12 to the bottom portion 52 (see FIGS. 4 and 4A). In this way, the operative engagement between flap 26 and wheel 20 is similar to a ratchet and pawl mechanism. In such embodiments, flap 26 may be hingedly connected to bottom surface 15b of lid 15 at pivot edge 28, with opposite free edge 30 being unattached to lid 15 and thus free to pivot down from the underside of lid 15. As illustrated, flap 26 is preferably arranged such that pivot edge 28 is positioned closer to the proximal edge 70 of sliding lid 15 than free edge 30. In this way, the flap 26 is orientated to rotate wheel 26 when the sliding lid 15 is closed and thus after pharmaceutical waste has been deposited into the container. In certain embodiments, the hinged connection at edge 28 limits the pivoting movement of flap 26, such that flap 26 is not capable of a full range of motion. In the illustrated embodiment, the hinged connection allows for flap 26 to pivot down a maximum angular distance D from a top position 40 adjacent the underside of lid 15 to a pivoted position 42. In certain embodiments, the angular distance D is less than 45 degrees. However, it is contemplated that the container may be designed different, with the pivoting distance of the flap being greater or less than the illustrated distance D as would generally occur to one skilled in the art.

Due to gravitational force or another appropriate type of force, such as spring force, flap 26 is urged to pivot or fall away from the underside of lid 15 to position 42 (see FIG. 4A). When lid 15 is moved from the closed position (FIG. 1) to the open position (FIG. 2), flap 26 will be pulled over paddles 22, with the paddles being substantially rigid to urge the flap up toward the underside of lid 15 at or near position 40. After flap 26 passes over a paddle 22, flap 26 will pivot downward and return to the downward or pivoted position 42. Thereafter, when lid 15 is moved from the open position to the closed position, flap 26 remains in pivoted position 42 and edge 30 consequently contacts at least one paddle 22. As the lid is closed, flap 26 will urge or move the proximal paddle 22, thereby turning wheel 20. As such, the solid pharmaceutical waste that has been deposited into container body 11 through opening 12 and gathered on wheel 20 will fall to the bottom of container body 11 as the wheel rotates. Flap 26 may be composed of a substantially rigid material, such as metal as an example, such that flap 26 is able to turn wheel 20 and will not deform against paddles 22 under the force applied to close lid 15. Optionally, wheel 20 may include tabs 46 angled from the distal edges 22b of each paddle 22. In such embodiments, flap 26 may catch underneath a tab 46 of a paddle 22 to further ensure that contact is made between flap 26 and the respective paddle 22 and the respective paddle is moved to rotate wheel 20 as lid 15 is closed. In addition to and/or in lieu of flap 26 rotating wheel 20 as lid 15 is closed, a user may also rotate wheel 20 by turning knob 17 to move the solid pharmaceutical waste to the bottom portion 52. In some embodiments, container 10 may also optionally include dissolving liquid in the bottom portion 52 to substantially dissolve tablets and capsules which are deposited into container 10. Such embodiments will further lower or eliminate the ability of an unapproved individual removing deposited solid pharmaceutical waste from container 10.

In certain embodiments, upper portion 50 and removable lower portion 52 meet at a joint 55. In this way, the interior cavity 60 of upper portion 50 is open to the interior cavity 62 of lower portion 52 such that solid pharmaceutical waste which has been deposited onto wheel 20 through opening 12 will accumulate in lower portion 52. As the waste accumulates, a user may desire to empty the collected waste and reuse container 10. Accordingly, lower portion 52 may be selectively removed from upper portion 50 to dispose of the solid pharmaceutical waste which has accumulated in lower portion 52. In certain embodiments, container 10 may also include a removal lid configured to be placed on the top of lower portion 52 after lower portion 52 is separated from container body 11. The lid (not shown) may be configured to snap fit onto portion 52 to close the lower portion. It is contemplated that the lower portion 52 may be reattached to upper portion 50 after the contents in lower portion 52 have properly disposed of. In other embodiments, it is contemplated that lower portion 52 may be disposable and thus disposed of after a certain amount of waste has accumulated therein. In such cases, a new lower portion 52 may be attached to upper portion 50 after the previous lower portion has been disposed of.

The upper and lower portions may fit together in numerous possible ways as would generally occur to one skilled in the art. In the illustrated embodiment, housing 51 has a bottom edge 80 configured to engage an upper edge 82 of housing 53. As an example, the edges may be keyed together via a mortise and tenon joint. As another example, one of the portions may include a perimeter rail configured to be positioned within a channel defined in the perimeter of the other portion. As yet another example, the portions may be selectively attached through the use of fasteners.

Turning to FIGS. 5A and 5B, container 110 is an example embodiment of a liquid pharmaceutical waste container according to the present disclosure. Container 110 generally includes a container body 111 defining a top opening 112 and a lid 115 configured to close the opening. Lid 115 is preferably composed of a penetrable material, such as rubber as an example, through which a needle can penetrate so that the liquid therein can be discharged from the needle into container body 111. FIG. 5B illustrates an example syringe 120 with a needle 121 that a user can insert or puncture or penetrate through lid 115 and then discharge the injectable from syringe 120 into the interior of container body 111. In certain embodiments, absorbent material can optionally be placed within the container body 111 to absorb the liquid injectable discharged into body 111. The absorbent material can be paper or clay based materials, as examples.

In the illustrated embodiment, lid 115 is connected to container body 111 via a strap 116. However, it should be appreciated that lid 115 can be unconnected to container body 111 when removed and/or can be connected to container body 111 in various other appropriate manners as would generally occur to one skilled in the art, including via a hinging assembly as an example. In yet other embodiments, lid 115 is not removable from container body 111 and a different access mechanism is optionally included in container body 111 for accessing the liquid pharmaceutical waste deposited into container 110.

In certain embodiments, containers 10 and 110 can be used in conjunction with sharps containers as a collective pharmaceutical waste containment and disposal system. Additionally, in certain embodiments, containers 10 and 110 can be provided in a larger box which is capable of being locked to further prevent unwanted access to the pharmaceutical waste.

In certain embodiments, one or more of containers 10 and 110 could optionally include additional features as would generally occur to one skilled in the art. As examples, one or more of the containers could include handles for carrying, transporting and positioning the containers, wheels disposed on the bottom surfaces of the containers for ease of movement of the containers, covers configured to cover portions or all of the containers as desired, and/or indicia representing entities responsible for disposing of the pharmaceutical waste collected within the containers and providing contact information for such entities. Additionally, in certain embodiments, one or both of containers 10 and 110 could optionally be sufficiently secured to the support surface upon which they rest to substantially prevent an unauthorized individual from removing the containers. In certain embodiments, bolts may be used to secure one or both of the containers to a support surface such as a floor surface, a wall surface, a cabinet, a countertop, etc.

In certain embodiments, the pharmaceutical waste which has accumulated in the containers may be emptied from the containers and collected by an appointed individual, department, company and/or government official so that the waste may be properly disposed of by an appropriate entity such as a pharmaceutical waste company, thereby preventing the pharmaceutical waste from being disposed of in other less desirable manners. In such cases, the containers may be reused after the accumulated waste has been emptied and collected. In other embodiments, the containers themselves may be safely transported to one or more disposal sites by appointed and approved individuals where the pharmaceutical waste contents may be released. In such cases, the containers may optionally be returned to the user and reused. Alternatively, the containers may be disposable after each use such that a user would require a new container after each container is filled and collected. In certain embodiments, the containers may be composed of a recyclable plastic material and may be recycled after one or multiple uses.

While the disclosure has been illustrated and described in detail in the drawings and foregoing description, the same is to be considered as illustrative and not restrictive in character, it being understood that only the preferred embodiment has been shown and described and that all changes and modifications that come within the spirit of the disclosure are desired to be protected.

What is claimed is:

1. A pharmaceutical waste disposal device, comprising:
    an upper portion adapted for receiving pharmaceutical waste and a lower portion adapted for collecting the pharmaceutical waste, the lower portion being selectively and removably engagable with the upper portion; wherein the upper portion includes:
        a hollow housing having an interior surface defining an internal cavity, an exterior surface, a length and a width, the housing defining respective top and bottom openings in communication with the internal cavity, the housing being configured to selectively engage with the lower portion, the top opening being divisible into adjacent respective first and second portions, the first and second portions each extending the length of the housing and collectively extending the width of the housing;
        a rotating wheel positioned within the housing, wherein the rotating wheel includes a plurality of paddles extending radially from a central rotating shaft, each of the paddles having a proximal edge rigidly engaged with the shaft and an opposite distal edge;
        a non-movable cover engaged with the housing at the top opening and positioned to cover the first portion of the top opening;
        a sliding lid engaged with the housing at the top opening and positioned to selectively cover the second portion of the top opening when at a closed position, the lid being configured to slide underneath the non-movable cover to an open position to reveal the second portion and provide access to the internal cavity therethrough, the sliding lid being configured to slide along the width of the housing, the sliding lid having opposing respective top and bottom surfaces; and
        a flap hingedly engaged with the sliding lid adjacent the bottom surface of the lid, wherein the flap includes a pivot edge hingedly engaged with the sliding lid and an opposite free edge movable within the internal cavity, the pivot edge being positioned closer to the non-moveable cover than the free edge when at the closed position, the flap being configured to pivot downward from the bottom surface an angular distance to a pivoted position, whereby sliding the lid from the open position toward the closed position causes the free edge to contact at least one of the paddles and urge the paddle to rotate the wheel to deposit pharmaceutical waste accumulated on the wheel into the lower portion;
    wherein the lower portion includes a hollow housing defining an internal cavity and a top opening in communication with the internal cavity, wherein the hollow housing of the lower portion is configured to selectively engage with the hollow housing of the upper portion so that the internal cavity of the upper portion is in communication with the internal cavity of the lower portion when the top and lower portions are engaged.

2. The device of claim 1, further comprising a turning knob positioned on the exterior surface of the housing of the upper portion, the knob being operatively coupled with the central rotating shaft and operable to rotate the rotating wheel when turned by a user.

3. The device of claim 1, wherein the central rotating shaft extends the length of the housing of the upper portion and each of the paddles has a length extending substantially the length of the housing of the upper portion to substantially prevent access to the interior cavity of the lower portion through the top opening of the upper portion.

4. The device of claim 1, wherein the distance from the distal edge of one of the paddles to the distal edge of the radially opposite paddle is substantially equal to the width of the housing of the upper portion.

5. The device of claim 1, wherein the sliding lid includes opposing sliding edges and each of the sliding edges includes at least one roller configured to translate within a corresponding guide rail disposed on the housing of the upper portion.

6. The device of claim 1, wherein the sliding lid includes opposing sliding edges configured to translate within corresponding channels defined in the housing of the upper portion.

7. The device of claim 1, wherein the rotating wheel includes angled tabs extending from each of the distal edges of the paddles, the angled tabs being configured to catch the free edge of the flap to maintain contact between the flap and the respective paddle.

8. The device of claim 1, wherein the lower portion contains an amount of dissolving liquid operable to at least partially dissolve the pharmaceutical waste collected in the lower portion.

9. The device of claim 1, wherein the rotating wheel includes rubber tips positioned at the distal edges of the paddles, the rubber tips configured to slide along part of the interior surface of the housing of the upper portion.

10. The device of claim 1, wherein the angular distance is less than 45 degrees.

11. The device of claim 1, wherein the flap is composed of a substantially rigid material.

12. A method, comprising:
   sliding open the lid of a pharmaceutical waste container, the waste container having an upper portion for receiving pharmaceutical waste and a lower portion for collecting the pharmaceutical waste, the upper portion of the container having an internal rotating wheel, the lid being selectively engageable with the wheel such that sliding the lid closed operates to rotate the wheel;
   depositing pharmaceutical waste into the upper portion of the waste container; and
   sliding the lid of the waste container closed, thereby rotating the wheel to transfer the deposited pharmaceutical waste into the lower portion of the container.

13. The method of claim 12, further comprising:
   removing the lower portion of the container from engagement with the upper portion; and
   discarding the pharmaceutical waste collected in the lower portion of the container.

14. The method of claim 13, further comprising disposing of the lower portion of the container and providing a second, unused lower portion and engaging the second, unused lower portion with the upper portion of the container.

15. The method of claim 13, further comprising re-engaging the lower portion of the container with the upper portion of the container.

16. The method of claim 13, further comprising turning a knob on the pharmaceutical waste container to rotate the wheel.

17. The method of claim 13, further comprising placing an amount of dissolving liquid in the lower portion of the container to at least partially dissolve the deposited pharmaceutical waste.

18. A pharmaceutical waste disposal device, comprising:
   an upper portion adapted for receiving pharmaceutical waste and a lower portion adapted for collecting the pharmaceutical waste, the lower portion being selectively and removably engagable with the upper portion;
   wherein the upper portion includes a housing surrounding an internal rotating wheel and a lid slideably engaged with the housing, wherein the rotating wheel includes collection areas adapted for collecting pharmaceutical waste placed in the upper portion, wherein the lid includes a lower pivoting flap adapted for contacting and rotating the wheel upon sliding closing of the lid to transfer the pharmaceutical waste to the lower portion;
   wherein the rotating wheel is sized and positioned within the housing in a manner to substantially prevent access to the pharmaceutical waste collected in the lower portion.

19. The device of claim 18, wherein the rotating wheel includes a plurality of paddles extending radially from a central rotating shaft, each of the paddles having a proximal edge rigidly engaged with the shaft.

20. The device of claim 19, further comprising a turning knob operatively coupled with the central rotating shaft and operable to rotate the wheel when the knob is turned.

* * * * *